United States Patent
Barth

(10) Patent No.: US 8,099,995 B2
(45) Date of Patent: Jan. 24, 2012

(54) CHOKED FLOW ISOLATOR FOR NOISE REDUCTION IN ANALYTICAL SYSTEMS

(75) Inventor: Phillip W. Barth, Portola Valley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 491 days.

(21) Appl. No.: 12/335,842

(22) Filed: Dec. 16, 2008

(65) Prior Publication Data

US 2010/0147050 A1    Jun. 17, 2010

(51) Int. Cl.
*G01N 30/38* (2006.01)
(52) U.S. Cl. ............... 73/23.42; 95/82; 96/101
(58) Field of Classification Search .......... 73/23.35, 73/23.42; 95/82; 96/101; 422/89
See application file for complete search history.

(56) References Cited

U.S. PATENT DOCUMENTS

| | | | |
|---|---|---|---|
| 4,244,396 A | | 1/1981 | Friedland et al. |
| 4,341,108 A | * | 7/1982 | Warncke et al. ............... 73/23.2 |
| 5,487,312 A | * | 1/1996 | Kahl et al. ................. 73/863.01 |
| 7,511,802 B2 | * | 3/2009 | Smith ............................. 356/72 |

OTHER PUBLICATIONS

Bally, R.W. et al., "Tapered Versus Constant Diameter Post-Column Restrictors in Capillary SFC", Journal of High Resolution Chromatography & Chromatography Communications, vol. 9, Nov. 1986, pp. 626-632.*

* cited by examiner

*Primary Examiner* — Daniel Larkin

(57) ABSTRACT

An apparatus and a method of making a measurement using the same. The apparatus includes a channel through which a fluid flows, a detector, and a choked flow channel. The detector measures a property of the fluid by generating a signal that depends on that property. The signal generated also depends on a pressure of the fluid in the detector. The choked flow channel receives the fluid at a first pressure after the fluid has been measured by the detector, and then transmits the fluid to a downstream location at a second pressure. The fluid reaches a supersonic velocity at one point in the choked flow channel. The choked flow channel may include a convergent-divergent nozzle or an orifice in a structure located in the choked flow channel.

20 Claims, 4 Drawing Sheets

CHOKED FLOW ISOLATOR FOR NOISE REDUCTION IN ANALYTICAL SYSTEMS

BACKGROUND OF THE INVENTION

Gas chromatographs are used to separate mixtures of gaseous compounds into the individual components and then measure the concentration of each component. The sample to be analyzed is injected into a separation column in a carrier gas that flows through the column. The time needed for a particular chemical component to traverse the column depends on the interactions between the component and the column material. Hence, the components are separated in space as the components move through the column and exit the column at different times. The amount of material leaving the column is measured by some form of detector to provide an analysis of the original sample. The gas then exits the system.

Gas chromatographs often utilize detectors that measure the thermal conductivity of the gas leaving the column. The detectors respond to the changes in thermal conductivity of the gas, and hence, are sensitive to the pressure of the gas at the detector, because thermal conductivity of a gas increases with pressure of the gas. As the sensitivity of the detectors has improved, the sensitivity of the detectors to "noise" resulting from intermittent pressure changes in the room containing the chromatograph has become a problem. For example, if the carrier gas is vented into the room in which the chromatograph is located, pressure fluctuations in the room resulting from doors being opened and closed, or from people moving about the room, are transmitted back to the detector through the gas discharge line. Similarly, if the gas is drawn through the chromatograph and into a disposal cylinder by a vacuum pump, fluctuations in the pump pressure can also be transmitted back to the detector and alter the readings made by the detector.

SUMMARY OF THE INVENTION

The present invention includes an apparatus and a method for making a measurement using the same. The apparatus has a channel through which a fluid flows, a detector, and a choked flow channel. The detector measures a property of the fluid by generating a signal that depends on that property. The signal generated also depends on a pressure of the fluid in the detector. The choked flow channel receives the fluid at a first pressure after the fluid has been measured by the detector, and then transmits the fluid to a downstream location at a second pressure. The fluid reaches a supersonic velocity at one point in the choked flow channel. In one embodiment, the choked flow channel includes a convergent-divergent nozzle. In another embodiment, the choked flow channel includes an orifice in a structure located in the choked flow channel. The present invention may be used in a gas chromatography system or in other systems, for example in detecting the carbon dioxide concentration in flue gases.

DETAILED DESCRIPTION OF THE PREFERRED EMBODIMENTS OF THE INVENTION

Figure 1:
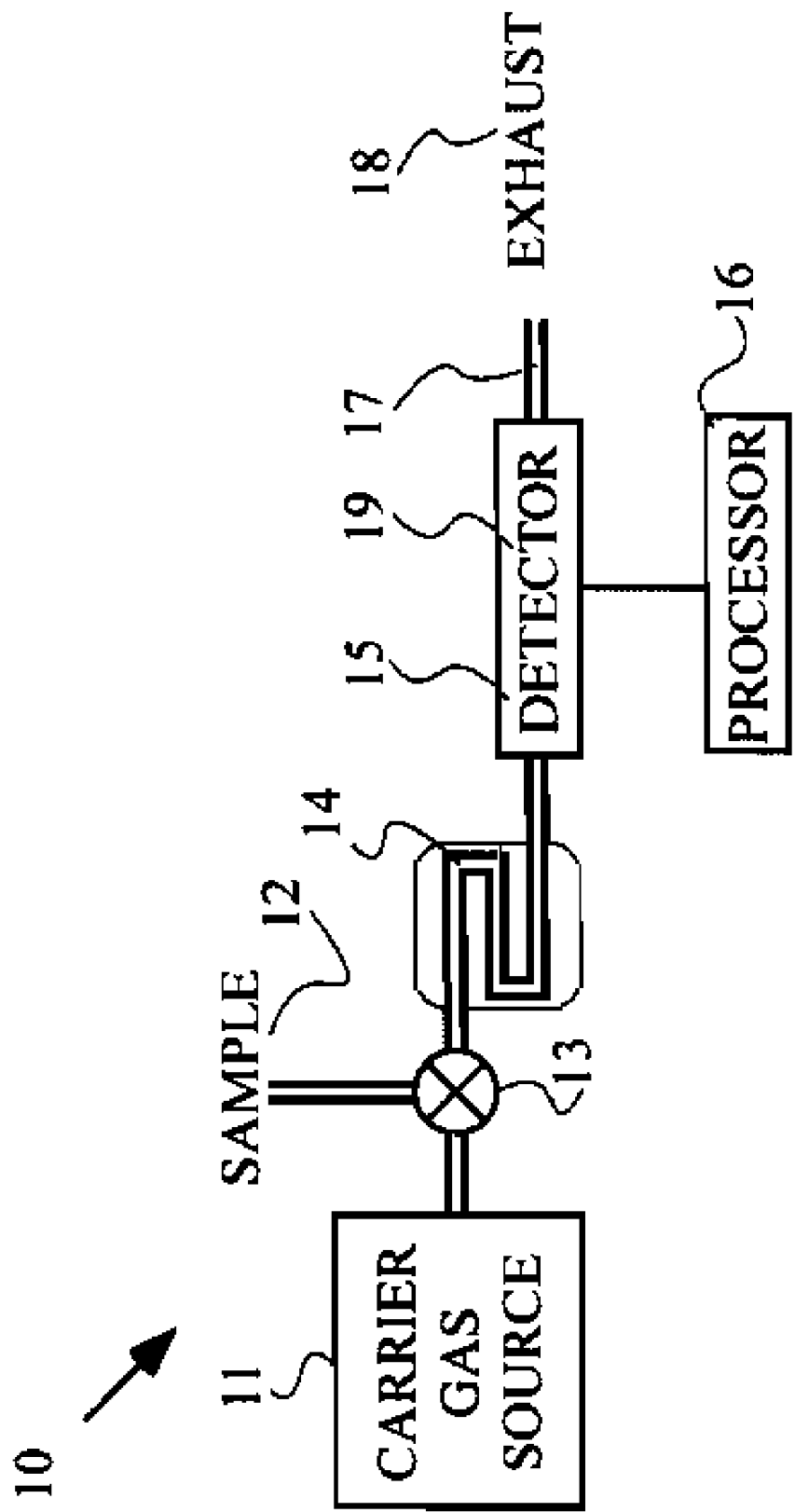
FIG. 1 is a simplified block diagram of a prior art gas chromatograph.

The manner in which the present invention provides its advantages can be more easily understood with reference to FIG. 1, which illustrates a prior art gas chromatograph 10. Gas chromatography is used in analytical chemistry for the separation and measurement of the constituents of a gaseous sample. Gas chromatograph 10 operates by injecting a sample comprising multiple constituents into a carrier gas that flows from a source 11 through a column 14 that separates the constituents of the sample such that different constituents exit column 14 at different times. The sample is injected into the carrier gas from a source 12 with the aid of an injection valve 13. The sample is injected in a short pulse into the continuously flowing carrier gas. The carrier gas is typically an inert gas such as helium.

Column 14 is typically a capillary, for example a fused quartz capillary, that is lined on its interior wall with a material that is capable of absorbing and desorbing each of the constituents of the gaseous sample. The migration rate of each constituent of the sample along the length of the column depends on the carrier gas velocity and the degree to which that constituent is absorbed by the material in column 14. Hence, the output of column 14 is a series of constituent vapor peaks in carrier gas separated by regions of pure carrier gas.

The output gas stream from column 14 is passed through a detector 15 that measures a specific property of the gas stream, usually with the aid of an electronic processor 16. One type of analyzer is a thermal conductivity detector (TCD), which measures the thermal conductivity of the gas stream, which measurement can be used to determine the concentration or mass of the sample gas in the carrier gas. The detector output is a series of peaks that can be analyzed to determine the identity and concentration of the constituents of the gas sample that was injected into the carrier gas. The gas stream exits the detector as gas flow 17 and is exhausted to the environment at an environmental pressure 18. Any disturbances in the environmental pressure 18 can propagate upstream and can affect the pressure at location 19 in detector 15, possibly disturbing the desired measurement by detector 15.

Figure 2:
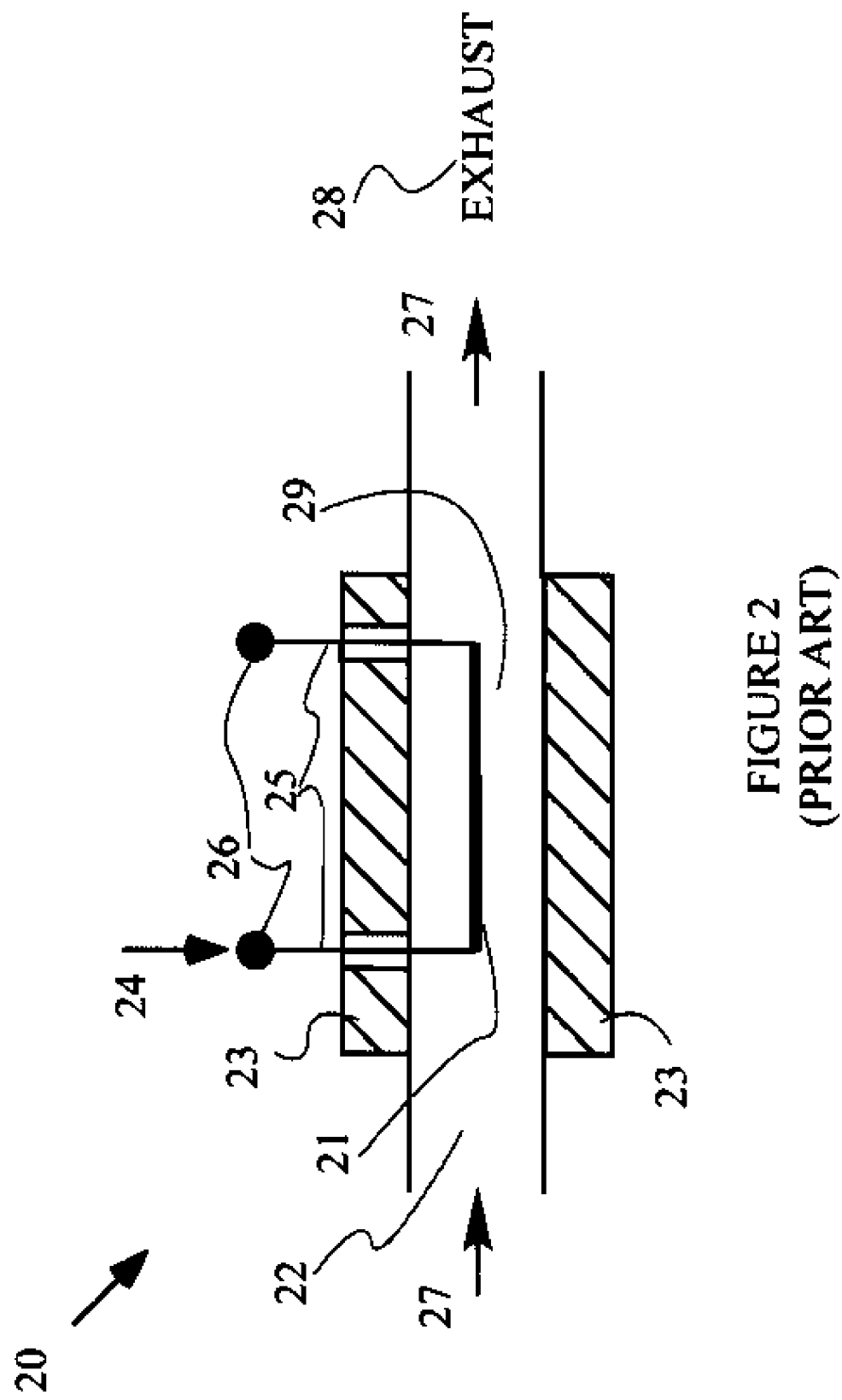
FIG. 2 is a simplified cross-sectional view of a prior art thermal conductivity detector.

A representative TCD 20 is illustrated in FIG. 2. Such a TCD may be used as the detector 15 as shown in FIG. 1, and may be constructed, for example, as an electrically heated resistive wire 21 in a channel 22 having a wall 23 cooler than heated wire 21. Wire 21 is heated by causing an electrical current 24 to flow through wire 21 via electrical leads 25 by introduction at electrical terminals 26. Wire 21 reaches an equilibrium temperature when the heat generated by the electrical current passing through wire 21 is balanced by the heat transferred through the thermally conductive gas flow 27 passing along and around the wire. This heat is transferred from wire 21 to wall 23, which is cooler than wire 21. The equilibrium temperature of wire 21 is measured by measuring the electrical resistance of the wire 21. Wire 21 is constructed from a material such as tungsten such that the change in temperature results in a measurable resistance change as the composition of the gas passing over the wire changes.

Any change in the mass or composition of gas flow 27 flowing over the resistor alters the thermal conductivity of the gas and so alters this thermal equilibrium temperature. Such changes occur when time-separated constituents of the input sample exit column 14 and are introduced to detector 20 as part of gas flow 27. Hence, by monitoring the voltage across wire 21 at terminals 25 in an appropriate electrical circuit, the concentrations of the constituents can be measured.

The gas flowing through detector 20 must exit the system as exhaust after flowing through the detector. This gas is typically vented to the surrounding environment at an environmental pressure 28. Any pressure disturbances that are present in the environment at the exit port of the detector 20 can propagate up the flow channel from the environment to wire 21, thus altering the pressure at location 29 within the detector. Unfortunately, fluctuations in the pressure at location 29 of the gas 27 within the detector 20 also cause fluctuations in the thermal conductivity of the gas, which in turn result in changes in the equilibrium temperature of the wire 21, and hence, introduce noise into the measurements. Such pressure disturbances may include acoustical waves, which can introduce short duration pressure fluctuations that interfere with the detector measurements.

The present invention is based on the observation that, since gas pressure fluctuations travel at or below the speed of sound, such fluctuations cannot be transmitted upstream against a supersonic gas flow. Thus, if the flow downstream of the detector can be made supersonic, the detector is isolated from the effects of downstream pressure fluctuations.

Figure 3:
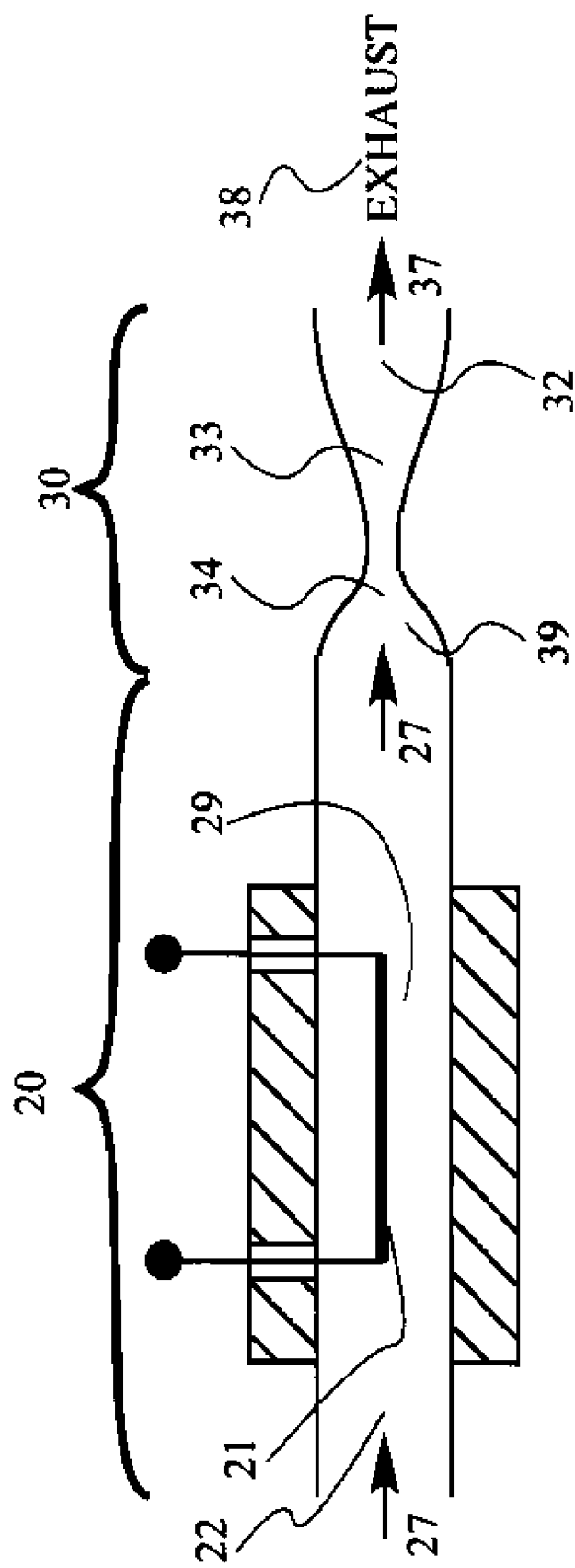
FIG. 3 is a simplified cross section of the thermal conductivity detector of FIG. 2 coupled to a convergent-divergent nozzle used to induce a "choked-flow" condition in one embodiment of the invention.

Refer now to FIG. 3, which is a cross-sectional view of a detector 20, as in FIG. 2, coupled directly to a convergent-divergent nozzle 30 according to one embodiment of the present invention. Detector 20 could be utilized as detector 15 in a gas chromatograph such as that shown in FIG. 1. Convergent-divergent (C-D) nozzle 30 is shown coupled directly to detector 20, but this direct coupling is not essential to practicing the invention. For example, the C-D nozzle could be placed at some distance downstream of detector 20. An additional detector or detectors could then be placed between detector 20 and C-D nozzle 30.

It should also be noted that a C-D nozzle can be retrofit to an existing instrument by adding the nozzle at the output port of the instrument. Hence, the existing instrument can be easily upgraded utilizing the present invention.

The dimensions of nozzle 30 and the pressure differential across nozzle 30 are chosen such that the gas velocity within nozzle 30 becomes supersonic at some point within the nozzle. When this condition of supersonic flow is achieved, pressure fluctuations at location 32 at the exhaust side of nozzle 30 cannot travel upstream against the supersonic flow at, for example, location 33 to upstream side 34, and thus the pressure at location 39 at the upstream side of the nozzle is unaffected by fluctuations in environmental pressure at location 38. The pressure at location 39 is determined by the pressure drop due to the flow of gas from the gas source to the detector, and hence, hot wire 21 is isolated from fluctuations in the environmental pressure at location 37. Accordingly, errors introduced by pressure fluctuations in the room or exhaust system of detector 20 are substantially reduced if not eliminated.

The embodiment shown in FIG. 3 utilizes a convergent-divergent nozzle to achieve the supersonic flow needed to block the upstream propagation of pressure fluctuations from the environment outside the flow channel. However, other structures that induce a "choked flow" condition could also be utilized. Choked flow occurs when a gas flows through a restriction from a higher pressure to a lower pressure. When the upstream pressure is above a predetermined value that depends on the gas and the temperature, the velocity of the gas in the restriction across which the pressure is maintained becomes supersonic and will not increase if the downstream pressure is decreased. In this case, the mass flow rate through the restriction is primarily a function of the upstream pressure and the upstream temperature. Accordingly, such a restriction also provides a flow regulator that determines the rate at which gas flows past hot wire 21.

In addition to a change in the cross-section of the flow channel, choked flow can be generated by Fanno flow, isothermal flow, or Rayleigh flow in the channel. In the case of Fanno flow, isothermal flow, and Rayleigh flow, the flow channel has a cross-sectional constant area, and the pressure and/or temperature are chosen such that the flow becomes supersonic at some point in the channel.

In a gas chromatograph incorporating the present invention, the pressure upstream of the choked flow point depends on the properties of the gas chromatograph channel and the pressures in the carrier gas source. Hence, this pressure cannot be freely varied. However, the pressure on the downstream side of the choked flow point can be controlled with a vacuum pump. The flow in the channel will become choked when the ratio of the pressures across the channel, e.g., the ratio of the pressure at location 39 to the pressure at location 32 shown in FIG. 3, is greater than a critical value that depends on properties of the carrier gas. In the case of helium, the critical pressure ratio is approximately 2.04. Hence, by decreasing the pressure at location 32 on the exit side of the choked flow point, the flow can be forced into the choked mode. It should be noted that decreasing the pressure further at location 32 does not result in a significant change in the rate of gas flow through the choked flow channel.

Figure 4:
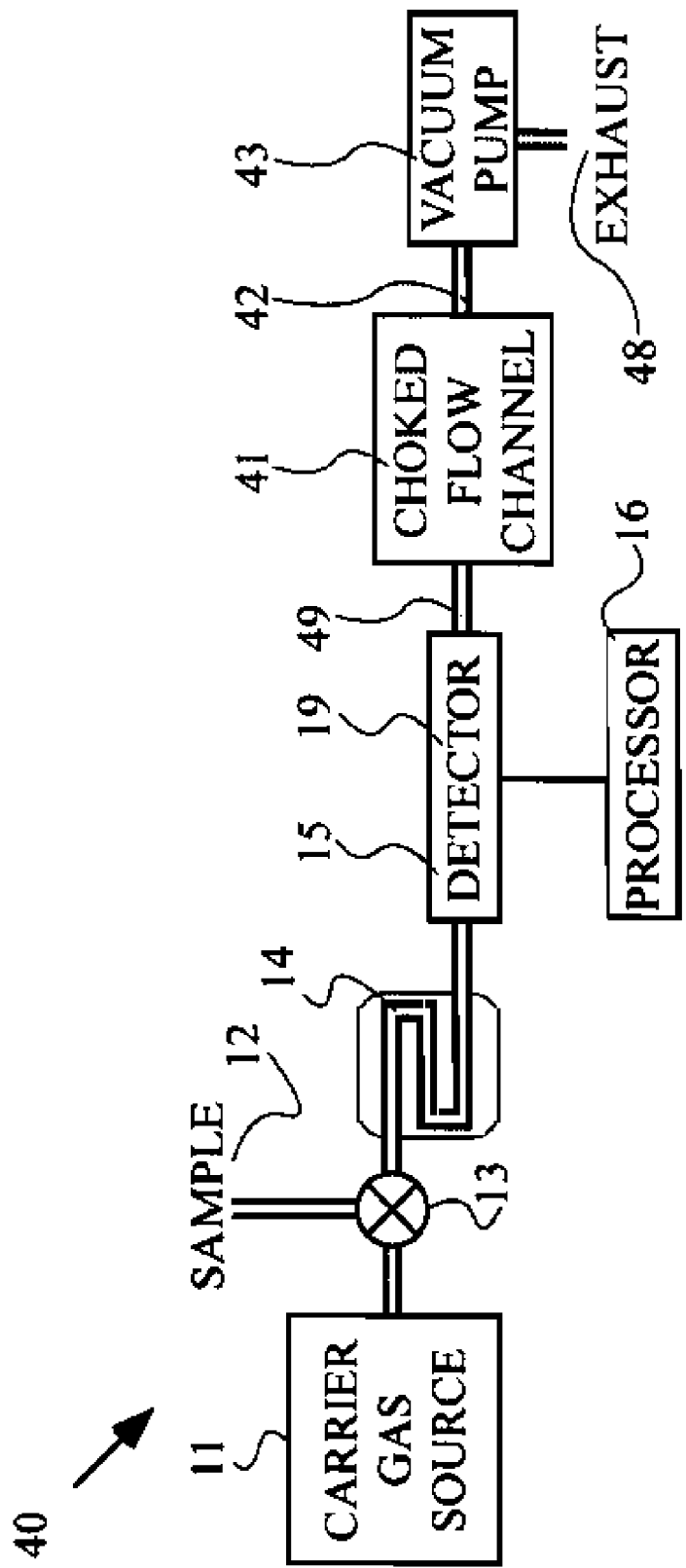
FIG. 4 is a simplified block diagram of a gas chromatograph according to one embodiment of the invention.

Refer now to FIG. 4, which is a cross-sectional view of a gas chromatograph according to one embodiment of the present invention. Components of gas chromatograph 40 that serve functions analogous to those described above in FIG. 1 have been given the same numerical designations and will not be discussed further here. Gas chromatograph 40 differs from gas chromatograph 10 in that a choked flow channel 41 has been introduced after detector 15. The upstream pressure in the channel at location 49 is set by the pressure supplied by carrier gas source 11 and by the flow resistance in column 14. The pressure at location 42 downstream of the choked flow channel is set by vacuum pump 43, which exhausts to the environmental pressure at location 48. The ratio of the upstream pressure in the channel at location 49 to downstream pressures at location 42 is maintained at a value greater than the critical value for the carrier gas being used. In one embodiment, helium is used as the carrier gas and the pressure ratio maintained at a value greater than 2.04. The flow rate in the gas chromatograph system is set by adjusting the pressure supplied by gas source 11. As long as the upstream to downstream pressure ratio remains greater than the critical value, pressure fluctuations resulting from pump 43 or variations in environmental pressure at location 48 are blocked from reaching detector 15. Thus for example if it is desired that the pressure at location 49 were 1 bar, then the pressure at location 42 must be less than 1/(2.04)=0.488 bar for supersonic flow to be achieved across choked flow channel 41. This level of 0.488 bar could be easily obtained with an inexpensive pump.

It will be appreciated that the presence of the vacuum pump 43 is not essential to the practice of the present invention. If, for example, no vacuum pump is present then the pressure at location 42 is equal to the environmental pressure at location 48, for example 1 bar, and the pressure at location 49 must then be greater than 2.04 bar for supersonic flow to be obtained.

The cross-sectional area of the choked flow channel may be chosen according to the desired flow through gas chromatograph column 14 and the desired pressures at locations 49 and 42, utilizing conventional gas flow models.

In one exemplary embodiment, the flow through the gas chromatograph system is 40 ml/minute referenced to standard temperature and pressure (STP) of 1 bar and 273K, the detector wall temperature is 400° C., and a pressure of about 1 bar is desired at the entrance to the choked flow channel. In this embodiment a C-D nozzle with a throat diameter of about 50 μm is used in conjunction with a vacuum pump that maintains the downstream pressure below 0.488 bar at the downstream end of the choked-flow channel.

In a second exemplary embodiment, the vacuum pump 43 is not used, and instead the pressure at location 42 equals the environmental pressure at location 48 of about 1 bar. If a flow of 40 ml/minute referenced to STP is desired, the detector wall temperature is 400° C., and pressure at location 49 is about 2.5 bar, which is above the critical pressure of 2.04 bar. Hence, for this embodiment, a C-D nozzle with a throat diameter of about 20 μm could be used.

The above-described embodiments utilize a thermal conductivity detector as the detector in the gas chromatograph system. However, the present invention can be advantageously applied to any gas chromatograph system in which the detector is sensitive to pressure fluctuations originating downstream of the detector. For example, a detector that measures the spectrographic properties of the gas can be sensitive to pressure fluctuations since the mass of gas in the spectrographic path increases with pressure. Similarly, detectors that measure the index of refraction of the gas are also pressure sensitive.

Similarly, the present invention can be applied to other instrument systems in which a fluid flows in a channel past a pressure sensitive detector, for example in detecting the presence of combustible gases in a spacecraft (see, for example, www.fire.tc.faa.gov/pdf/fsr-0185.pdf) or for detecting helium leaks in air (www.sigmaaldrich.com/Graphics/Sucelco/objects/4700/4696.pdf). By placing a choked flow channel downstream of the detector and maintaining the flow through the choked flow channel such that the flow is supersonic within the choked flow channel, the detector can be protected from pressure fluctuations originating downstream of the choked flow channel.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. An apparatus comprising:
a channel through which a fluid flows;
a detector for measuring a property of said fluid, said detector generating a signal that depends on said property and on a pressure of said fluid in said detector; and
a choked flow channel that receives said fluid at a first pressure after said fluid has been measured by said detector, said choked flow channel transmitting said fluid to a downstream location at a second pressure, said fluid reaching a supersonic velocity at one point in said choked flow channel.

2. The apparatus of claim 1 wherein said choked flow channel comprises a convergent-divergent nozzle.

3. The apparatus of claim 1 wherein said choked flow channel comprises an orifice in a structure located in said choked flow channel.

4. The apparatus of claim 1 wherein said choked flow channel comprises a Fanno flow channel, an isothermal flow channel, or a Rayleigh flow channel.

5. The apparatus of claim 1 wherein said fluid comprises a gas.

6. The apparatus of claim 1 further comprising an analysis channel upstream of said detector, said detector detecting a gas leaving said analysis channel.

7. The apparatus of claim 6 in which said analysis channel comprises a separation channel in a gas chromatograph.

8. The apparatus of Claim 1 wherein said detector comprises a thermal conductivity detector.

9. The apparatus of claim 1 further comprising a vacuum pump that sets said second pressure.

10. A method for making a measurement, said method comprising:
causing a fluid having a property that is to be measured to flow through a detector that generates a detector signal that depends on said property and on a pressure of said fluid in said detector;
causing said fluid to reach a supersonic velocity after leaving said detector and prior to said fluid arriving at a location at a second pressure that is subject to pressure variations; and
generating said measurement using said detector signal.

11. The method of claim 10 wherein said fluid flows through an isolation channel comprising a choked flow channel after leaving said detector.

12. The method of claim 10 wherein said fluid comprises a plurality of components and wherein said method comprises causing said fluid to flow through an analysis channel in which different ones of said components travel at different speeds through said analysis channel prior to said fluid flowing through said detector.

13. The method of claim 12 wherein said fluid comprises a gas.

14. The method of claim 13 wherein said analysis channel comprises a separation channel in a gas chromatograph.

15. The method of claim 10 wherein said second pressure is set by a vacuum pump connected to said choked flow channel.

16. A gas chromatograph comprising:
a carrier gas source that provides a carrier gas to a separation channel;
a sample injection port that injects a sample to be analyzed into said carrier gas prior to said carrier gas entering said separation channel;
a detector that measures a property of gas leaving said separation channel; and
a choked flow channel that receives gas leaving said detector at a first pressure and discharges said gas at a second pressure, said gas reaching a supersonic velocity at a point in said choked flow channel.

17. The gas chromatograph of claim 16 wherein said choked flow channel comprises a convergent-divergent nozzle.

18. The gas chromatograph of claim 16 wherein said choked flow channel comprises an orifice in a structure located in said choked flow channel.

19. The gas chromatograph of claim 16 further comprising a vacuum pump that sets said second pressure.

20. The gas chromatograph of claim 16 wherein said detector measures a thermal conductivity of said gas.

* * * * *